United States Patent
Igarashi

(10) Patent No.: US 9,877,657 B2
(45) Date of Patent: Jan. 30, 2018

(54) MEDICAL IMAGE PROCESSING APPARATUS

(71) Applicant: Toshiba Medical Systems Corporation, Otawara-shi (JP)

(72) Inventor: Takuma Igarashi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 117 days.

(21) Appl. No.: 14/643,088

(22) Filed: Mar. 10, 2015

(65) Prior Publication Data

US 2015/0250395 A1    Sep. 10, 2015

(30) Foreign Application Priority Data

Mar. 10, 2014 (JP) .................. 2014-046441

(51) Int. Cl.
*G06K 9/00* (2006.01)
*A61B 5/02* (2006.01)
(Continued)

(52) U.S. Cl.
CPC .......... *A61B 5/02007* (2013.01); *A61B 5/021* (2013.01); *A61B 5/026* (2013.01);
(Continued)

(58) Field of Classification Search
CPC .......... A61B 2034/105; A61B 5/02007; A61B 5/021; A61B 5/026; A61B 5/7278;
(Continued)

(56) References Cited

U.S. PATENT DOCUMENTS

| 8,386,188 B2† | 2/2013 | Taylor |
| 2012/0041318 A1 | 2/2012 | Taylor |
| 2016/0117819 A1† | 4/2016 | Taylor |

FOREIGN PATENT DOCUMENTS

| JP | 2007-289588 | 11/2007 |
| JP | 2012-24582 | 2/2012 |
| JP | 2013-534154 | 9/2013 |

OTHER PUBLICATIONS

James K. Min, et al., "Rationale and design of the DeFACTO (Determination of Fractional Flow Reserve by Anatomic Computed Tomographic AngiOgraphy) study" Journal of Cardiovascular Computed Tomography, vol. 5, No. 5, Sep./Oct. 2011, pp. 301-309.

(Continued)

*Primary Examiner* — Manuchehr Rahmjoo
(74) *Attorney, Agent, or Firm* — Oblon, McClelland, Maier & Neustadt, L.L.P.

(57) ABSTRACT

According to one embodiment, a medical image processing apparatus includes first specifier, second specifier, determiner and display controller. First specifier collates an ischemic region calculated from a blood vessel visualized into a three-dimensional image in a plurality of phases with a dominating region of the blood vessel, and specifies a culprit vessel in the ischemic region. Second specifier specifies a culprit stenosis in the culprit vessel based on a pressure index calculated from the blood vessel. Determiner determines a connection position to connect a bypass vessel that makes a detour around the culprit stenosis. Display controller displays the determined connection position on a display.

11 Claims, 14 Drawing Sheets

(51) Int. Cl.

| | |
|---|---|
| *A61B 5/021* | (2006.01) |
| *A61B 5/026* | (2006.01) |
| *A61B 5/00* | (2006.01) |
| *A61B 6/03* | (2006.01) |
| *A61B 6/00* | (2006.01) |
| *G06T 7/62* | (2017.01) |
| *A61B 34/10* | (2016.01) |

(52) U.S. Cl.
CPC ............ *A61B 5/7278* (2013.01); *A61B 6/032* (2013.01); *A61B 6/486* (2013.01); *A61B 6/503* (2013.01); *A61B 6/504* (2013.01); *A61B 6/507* (2013.01); *A61B 6/5217* (2013.01); *G06T 7/62* (2017.01); *A61B 2034/105* (2016.02); *G06T 2207/10081* (2013.01); *G06T 2207/30048* (2013.01); *G06T 2207/30104* (2013.01); *G06T 2207/30172* (2013.01)

(58) Field of Classification Search
CPC ......... A61B 6/032; A61B 6/486; A61B 6/503; A61B 6/504; A61B 6/507; A61B 6/5217; G06T 2207/10081; G06T 2207/30048; G06T 2207/301
See application file for complete search history.

(56) References Cited

OTHER PUBLICATIONS

Jin-Ho Choi, et al., "Intracoronary Transluminal Attenuation Gradient in Coronary CT Angiography for Determining Coronary Artery Stenosis" JACC: Cardiovascular Imaging, vol. 4, No. 11, Nov. 2011, pp. 1149-1157.

† cited by third party

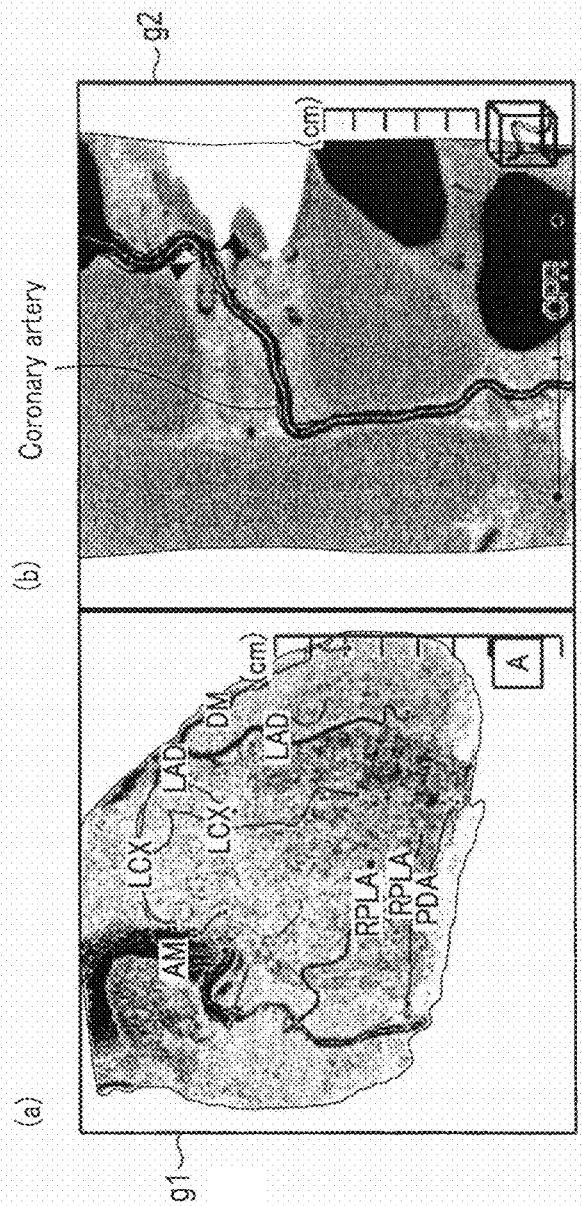
F I G. 4

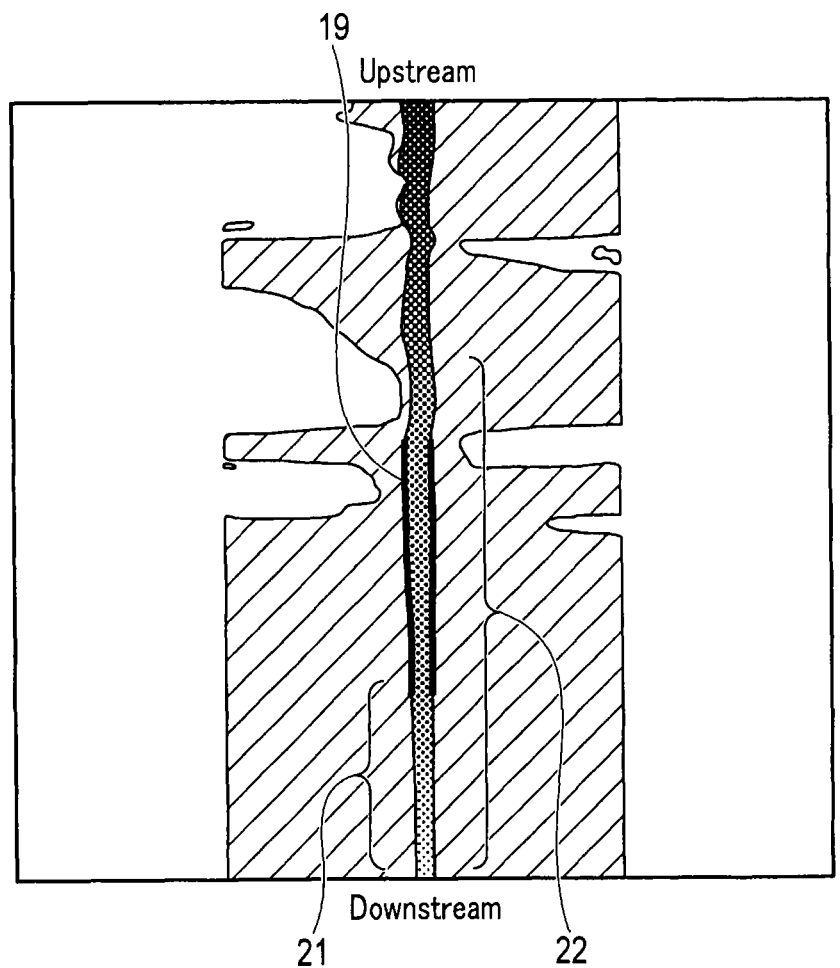
F I G. 10

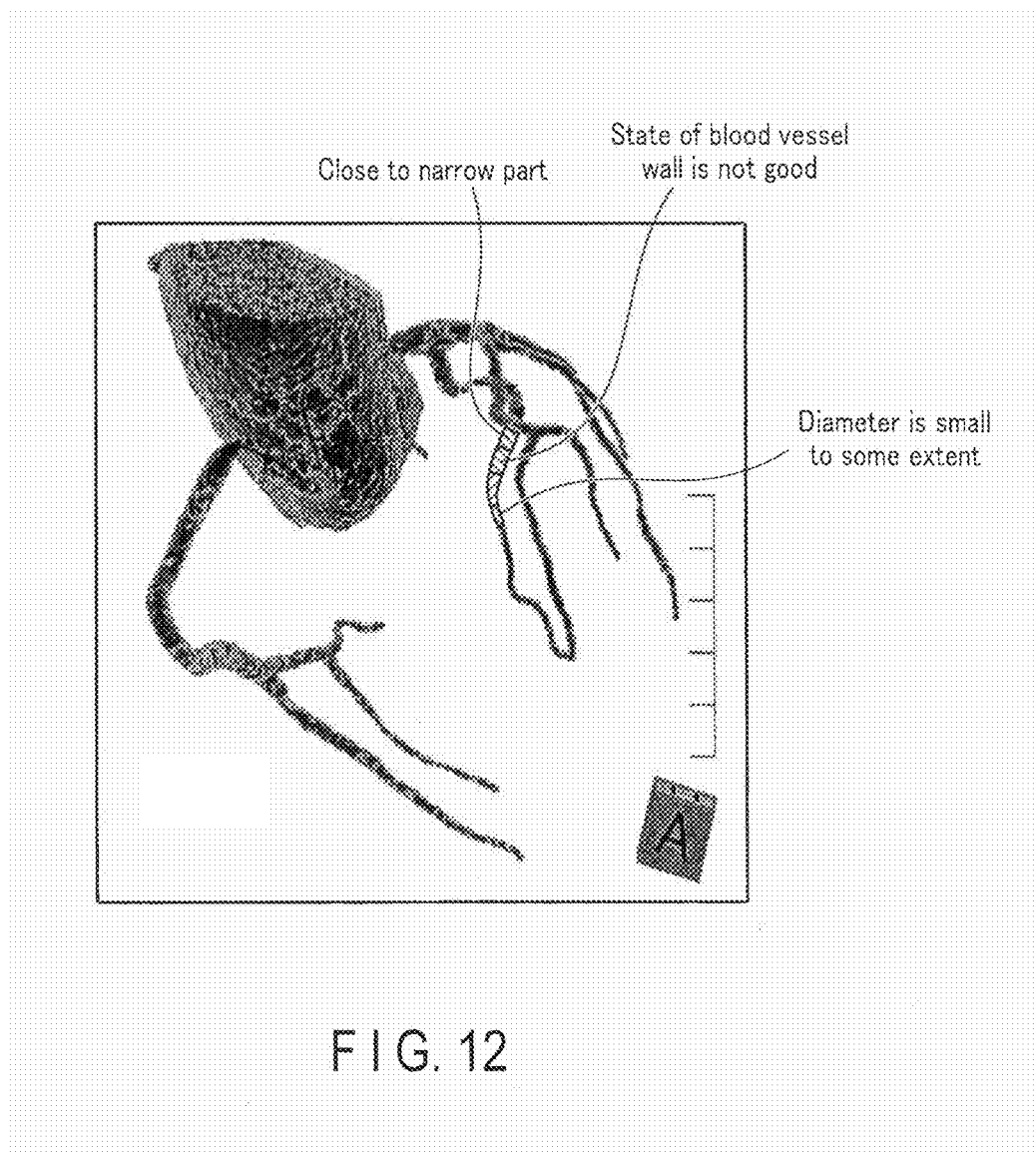
F I G. 12

MEDICAL IMAGE PROCESSING APPARATUS

CROSS-REFERENCE TO RELATED APPLICATIONS

This application is based upon and claims the benefit of priority from the Japanese Patent Application No. 2014-046441, filed Mar. 10, 2014, the entire contents of which are incorporated herein by reference.

FIELD

Embodiments described herein relate generally to a medical image processing apparatus.

BACKGROUND

In ischemic heart diseases, coronary occlusion or stenosis impedes the blood flow to the cardiac muscle. Shortage or stop of the blood supply to the cardiac muscle leads to heart disorders. Patients complain of pain or oppressive feeling in the precordia, left arm, or back. A patient suffering from a disease of this type may be treated with one of pharmacotherapy, PCI (catheterization), and bypass operation.

In the pharmacotherapy, the patient is administered a drug to improve the ischemia in the heart or prevent formation of blood clots.

In the PCI, a thin tubular treatment instrument is directly inserted into a blood vessel in which occlusion or stenosis has occurred, thereby forcibly extending the blood vessel. However, if the coronary artery has an advanced three-vessel disease, chronic complete occlusion, or the like, it is difficult to conduct PCI.

The bypass operation is considered for a patient who is in a severe condition and cannot have a treatment by PCI. The bypass operation is a technique also called CABG (Coronary Artery Bypass Grafting).

In the CABG, a narrowed or occluded blood vessel is connected to another blood vessel (graft vessel) so as to flow the blood to the ischemic part via the graft vessel, as shown in FIGS. 14 and 15.

In FIG. 14, reference numeral 2 shows the Right coronary artery. Reference numeral 7 shows the Left coronary artery. Reference numeral 31 shows the Left main trunk. Reference numeral 9 shows the Circumflex artery. Reference numeral 10 shows the Anterior descending branch.

In FIG. 15, reference numeral 32 shows the Internal thoracic artery graft. Reference numeral 33 shows the Radial artery graft. Reference numeral 34 shows the Great saphenous vein graft.

The graft vessel is taken from the internal thoracic artery or great saphenous vein. When the internal thoracic artery is used, the incidence of restenosis is low, and the prognosis is good, as is known.

FFR (Fractional Flow Reserve) is an index used to select which one of PCI and pharmacotherapy is to be applied. The degree of progress of stenosis is inspected by, for example, directly inserting a pressure wire into a blood vessel. The pressure wire 35 is inserted into the blood vessel, as shown in FIG. 16, to measure pressures $P_{in}$ and $P_{out}$ before and after the narrow parts 36.

The FFR is defined by $P_{in}/P_{out}$. If the FFR is lower than 0.8, PCI is selected as the treatment. If higher, pharmacotherapy is selected. However, since inserting the pressure wire into the blood vessel is invasive, there is a demand for a noninvasive pressure measurement method and FFR estimation method.

There has been devised a method of calculating an FFR estimation value by a simulation. A technique of this type inputs a blood vessel shape acquired from modality and physical parameters such as the viscosity value of the blood or the like to a simulator. The FFR is estimated (calculated) by fluid analysis using Navier-Stokes equations used in CFD (Computational Fluid Dynamics).

An existing simulation uses a 3D image. However, since the 3D simulation needs a long calculation time, the simulation using a 3D image is 2D-approximated, thereby greatly shortening the time necessary for the simulation. This contrivance enables to quickly calculate the FFR on a simulation base. The FFR based on the approximate simulation is widely recognized as an effective index.

When CABG is selected as the treatment, it is necessary to determine the connection position of the graft vessel in the preoperative plan. The doctor confirms the state of the blood vessel by diagnostically interpreting medical images obtained by CTA (CT Angiography) or the like, and determines the connection position. However, it is difficult to interpret details of the blood vessel state. Hence, the interpreter is heavily burdened, and the possibility of oversight is undeniable. If a stenosis on the downstream side of the connection position is overlooked, the function of the cardiac muscle cannot recover, and the operation fails.

BRIEF DESCRIPTION OF THE DRAWINGS

FIG. 4 is a schematic view showing an example of the result of coronary artery analysis by the medical image processing apparatus 10 shown in FIG. 1;

FIG. 10 is a view showing an example of an SPR image including a connection position indicated by a marker;

FIG. 12 is a view showing an example of a three-dimensional image representing a connection position including a risk distribution;

DETAILED DESCRIPTION

In general, according to one embodiment, a medical image processing apparatus includes a first specifier, a second specifier, a determiner and a display controller. The first specifier collates an ischemic region calculated from a blood vessel visualized into a three-dimensional image in a plurality of phases with a dominating region of the blood vessel, and specifies a culprit vessel in the ischemic region. The second specifier specifies a culprit stenosis in the culprit vessel based on a pressure index calculated from the blood vessel. The determiner determines a connection position to connect a bypass vessel that makes a detour around the culprit stenosis. The display controller displays the determined connection position on a display.

Figure 1:
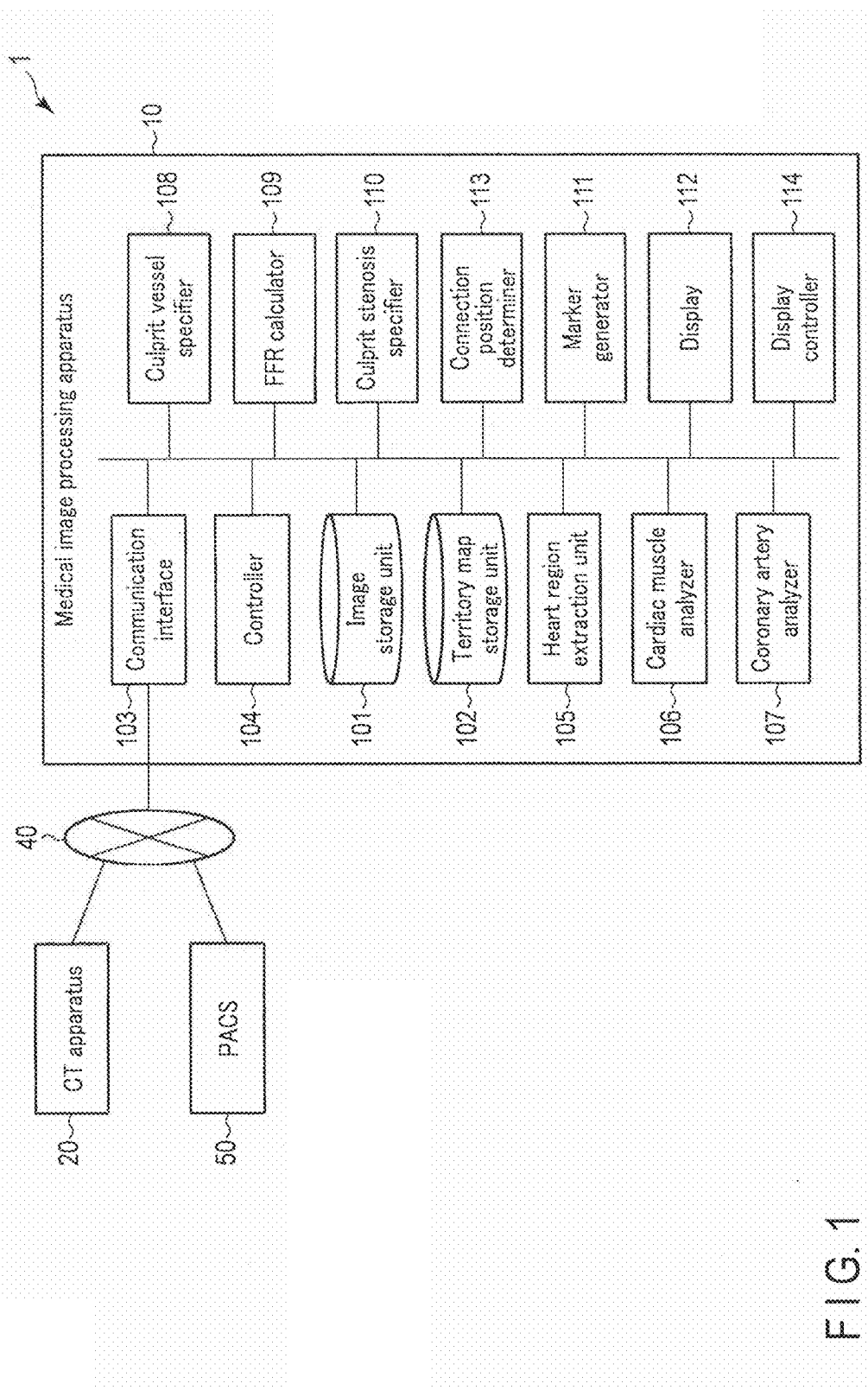
FIG. 1 is a functional block diagram showing an example of a medical image processing system including a medical image processing apparatus according to the embodiment.

FIG. 1 is a functional block diagram showing an example of a medical image processing system including a medical image processing apparatus according to the embodiment. A medical image processing system 1 shown in FIG. 1 includes a medical image processing apparatus 10, a CT (Computed Tomography) apparatus 20, and a PACS (Picture Archiving and Communication System) 50. The medical image processing apparatus 10, the CT apparatus 20, and the PACS 50 are communicably connected to each other via a network 40. The network 40 is, for example, a LAN (Local Area Network), a public electronic communication network, or the like.

In the embodiment, the medical image processing apparatus 10 can be used to make a preoperative plan of CABG based on the image data of a heart as an anatomical part. CABG is applied to a patient of an ischemic heart disease who meets, for example, conditions (1) to (4).

(1) The left main trunk is morbid (stenosis of 50% or more).

(2) PCI is difficult to conduct (due to advanced three-vessel disease, chronic complete occlusion, or the like)

(3) The blood flow in the peripheries of coronary arteries is excellent (blood vessel inner diameter >1.5 mm) (without stenosis/irregularity)

(4) The left cardiopulmonary function has the following state (ejection fraction (EF) is 20% or more, and left ventricle end diastolic pressure (LVEDP) is 20 mmHG or less)

An image storage unit 101 stores volume data transmitted from the CT apparatus 20 or the PACS 50 under the control of a controller 104. The volume data is, for example, time-series three-dimensional contrast CT image data over a plurality of phases concerning a chest region including the heart of an object.

Figure 2:
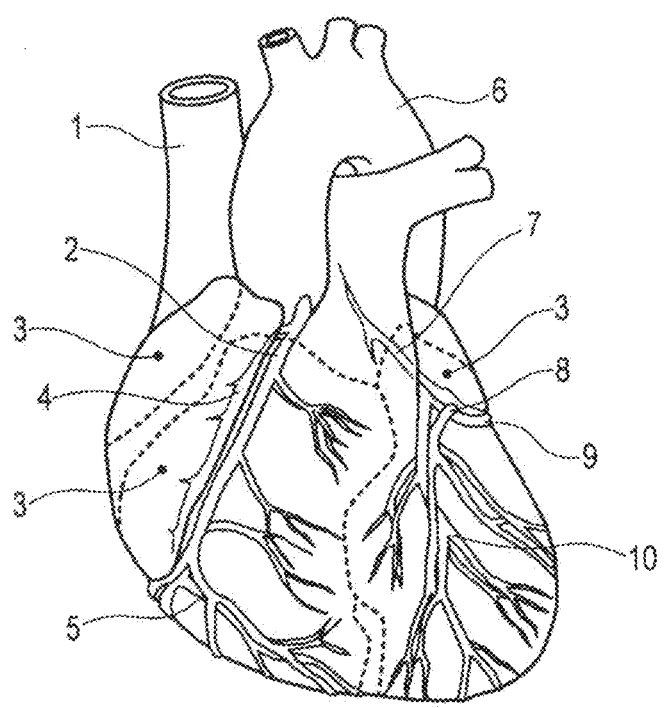
FIG. 2 is a schematic view showing an example of a territory map stored in a territory map storage unit 102 shown in FIG. 1.

A territory map storage unit 102 stores a territory map as shown in FIG. 2. The territory map (to be referred to as a dominating map hereinafter) is mapping data that defines the relationship between each coronary artery and the dominating region to which the coronary artery supplies nutrition.

In FIG. 2, reference numeral 1 shows the Superior vena cava. Reference numeral 2 shows the Right coronary artery. Reference numeral 3 shows the Dominating region. Reference numeral 4 shows the Anterior vein. Reference numeral 5 shows the Marginal branch. Reference numeral 6 shows the Aorta. Reference numeral 7 shows the Left coronary artery. Reference numeral 8 shows the Great cardiac vein. Reference numeral 9 shows the Circumflex artery. Reference numeral 10 shows the Anterior descending branch.

A communication interface 103 is connected to the network 40 to enable communication between the medical image processing apparatus 10 and the CT apparatus 20 or the PACS 50.

A heart region extraction unit 105 extracts a heart region from volume data by heart outline extraction processing or the like.

By, for example, threshold processing by a CT value corresponding to the contrast medium concentration, a cardiac muscle analyzer 106 extracts a cardiac muscle region from the heart region extracted by the heart region extraction unit 105. The cardiac muscle analyzer 106 also executes cardiac muscle perfusion analysis. That is, the cardiac muscle analyzer 106 generates a time concentration curve concerning the contrast medium for each pixel (or for each spot) in the extracted cardiac muscle region. The cardiac muscle analyzer 106 calculates, based on the time concentration curve, the blood flow that moves during the period from the inflow to the outflow of the contrast medium for each pixel (or for each spot).

For example, in imaging using the CT apparatus, the perfusion information of an organ can be visualized from a change in the CT value obtained by a nonionic contrast medium infused into the patient. Hence, according to CT perfusion analysis, a time-rate change in the CT image (volume data) formed from, for example, 512×512 pixels can be measured from a change in the CT value on a pixel basis, and the blood flow or the like can be expressed as numerical data based on the result. One color map representing the perfusion information (for example, blood flow) of the organ is thus generated from CT images in a plurality of phases.

In addition, the cardiac muscle analyzer 106 extracts an ischemic region from the spatial distribution of calculated blood flows by threshold processing.

A coronary artery analyzer 107 extracts a plurality of coronary arteries from the heart region extracted by the heart region extraction unit 105. The coronary artery analyzer 107 extracts at least one narrow part from each of the extracted coronary arteries. More specifically, the coronary artery analyzer 107 analyzes the anatomical structure of coronary arteries or the plaque properties along the center line or internal wall of each coronary artery, and extracts volume data about the coronary arteries. With this processing, each coronary artery and a narrow part located on the inner wall of the coronary artery are extracted.

Detailed examples of the plaque properties are a lipid, serum cholesterol level, hardness, calcification level, and fibrous coat (Thin-cap).

A culprit vessel specifier 108 specifies a culprit vessel by collating the ischemic region extracted by the cardiac muscle analyzer 106 with the dominating map (stored in the territory map storage unit 102). The culprit vessel is a blood vessel having a responsibility to supply nutrition to the ischemic region.

An FFR calculator 109 calculates, on a simulation base, an FFR value for each narrow part extracted by the coronary artery analyzer 107. More specifically, first, the FFR calculator 109 calculates tissue blood flows on the upstream and downstream of a narrow part for each narrow part extracted by the coronary artery analyzer 107 based on the color map generated by the cardiac muscle analyzer 106. The FFR calculator 109 then divides the calculated downstream tissue blood flow by the upstream tissue blood flow, thereby calculating the FFR of each narrow part.

The FFR is an example of a so-called pressure index. In addition, an index representing a change in the blood flow with respect to the axial direction of the blood vessel can be used as an index alternate to the FFR. For example, the connection position of a graft vessel can be determined using CFR (Coronary Flow Reserve). The CFR is the ratio of the blood flow in rest to the blood flow in maximum coronary vasodilation, and is defined by CFR=average pass time of thermal dilution curve in resting/average pass time of thermal dilution curve at the time of maximal hyperemia.

A culprit stenosis specifier 110 specifies, out of the narrow parts extracted by the coronary artery analyzer 107, a narrow part (to be referred to as a culprit stenosis hereinafter) located on the inner wall of the culprit vessel specified by the culprit vessel specifier 108. That is, the culprit stenosis specifier 110 specifies, out of several culprit stenosis candidates, a narrow part whose FFR is smaller than a threshold as a culprit stenosis.

A connection position determiner 113 determines a connection position (bypass portion) in the culprit vessel. That is, the connection position determiner 113 determines an appropriate position of the joint of a graft vessel (bypass vessel) on the culprit vessel based on index values such as an FFR drop level, the inner diameter of the blood vessel, and an elasticity coefficient (blood vessel elasticity).

A marker generator 111 generates the data of a marker used to visually display the connection position (determined by the connection position determiner 113) in addition to the culprit vessel (specified by the culprit vessel specifier 108), the culprit stenosis (specified by the culprit stenosis specifier 110), the FFR (calculated by the FFR calculator 109), and the culprit stenosis candidates (extracted by the coronary artery analyzer 107). The marker can be a symbolic graphic such as an arrow or a triangle, and can add a visual effect such as color mapping display or gradation.

A display controller 114 displays, on a display 112, a three-dimensional image generated from volume data by rendering or the like or a two-dimensional image generated by multi-planar reconstruction. The display controller 114 displays, on the display 112, an image generated by superimposing the marker generated by the marker generator 111 on the three-dimensional image or two-dimensional image. The processing procedure of the medical image processing apparatus 10 according to the embodiment will be described next.

Figure 3:
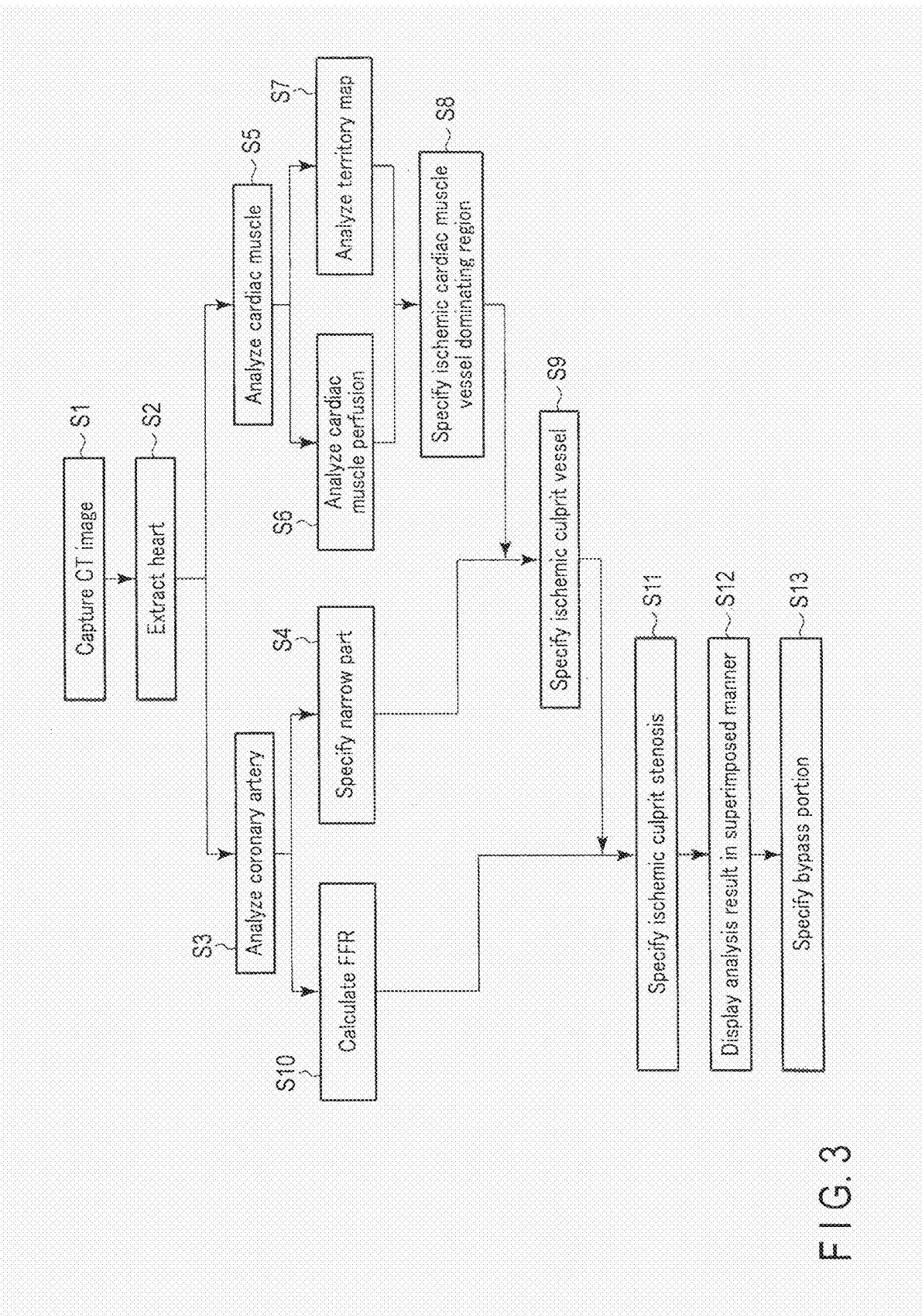
FIG. 3 is a flowchart showing an example of the processing procedure of a medical image processing apparatus 10 shown in FIG. 1.

FIG. 3 is a flowchart showing an example of the processing procedure of the medical image processing apparatus 10 shown in FIG. 1. Referring to FIG. 3, the controller 104 acquires time-series volume data over a plurality of phases concerning a chest region from the CT apparatus 20 or PACS 50 via the communication interface 103 (step S1). The acquired volume data is written in the image storage unit 101.

Next, the heart region extraction unit 105 reads out volume data of a predetermined phase including a relatively small number of pulsations from the image storage unit 101 under the control of the controller 104. The heart region extraction unit 105 extracts a heart region from the readout volume data (step S2).

The coronary artery analyzer 107 executes coronary artery analysis processing for the heart region extracted by the heart region extraction unit 105 (steps S3 and S4). More specifically, the coronary artery analyzer 107 analyzes the anatomical structure of coronary arteries or the plaque properties along the center line or internal wall of each coronary artery. Based on the result, the coronary artery analyzer 107 extracts each coronary artery and a narrow part located on the inner wall of the coronary artery.

The coronary artery analyzer 107 then superimposes the anatomical structure of the coronary arteries on the heart form image, thereby generating a three-dimensional image or two-dimensional image. The generated three-dimensional image or two-dimensional image is displayed on the display 112. FIG. 4 shows an example of a three-dimensional image g1 and an example of a two-dimensional image g2. The two-dimensional image g2 is, for example, a CPR (curved planar reconstruction) image. The user can arbitrarily set the timing of displaying the images g1 and g2 on the display 112. That is, the images can be displayed halfway through the processing or together with the processing result.

Next, the cardiac muscle analyzer 106 executes cardiac muscle analysis processing (step S5). By threshold processing using a CT value corresponding to the contrast medium concentration, the cardiac muscle analyzer 106 extracts a cardiac muscle region from the heart region extracted by the heart region extraction unit 105.

The cardiac muscle analyzer 106 then performs CT perfusion analysis processing for the extracted cardiac muscle region (steps S6, S7, and S8). More specifically, the cardiac muscle analyzer 106 generates a time concentration curve concerning the contrast medium for each pixel (or for each spot) in the extracted cardiac muscle region based on the time-series volume data. The cardiac muscle analyzer 106 then calculates, based on each time concentration curve, the blood flow that moves during the period from the inflow to the outflow of the contrast medium for each pixel (or for each spot).

Figure 5:
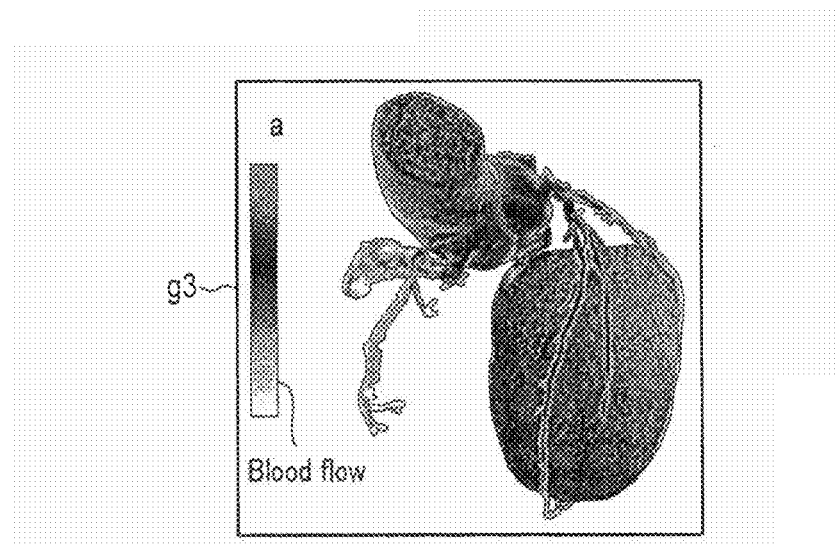
FIG. 5 is a schematic view showing an example of the result of cardiac muscle analysis by the medical image processing apparatus 10 shown in FIG. 1.

A color map g3 representing the spatial distribution of blood flows shown in, for example, FIG. 5 is thus generated. The cardiac muscle analyzer 106 extracts a region where the blood flow is less than a predetermined threshold as an ischemic region based on the generated color map g3 (that is, the spatial distribution of calculated blood flows).

The culprit vessel specifier 108 collates the specified ischemic region with the dominating map (for example, data shown in FIG. 2 which is stored in the territory map storage unit 102), thereby specifying a culprit vessel (step S9).

Based on the color map g3 generated by the cardiac muscle analyzer 106, the FFR calculator 109 calculates the tissue blood flow on the downstream side of each narrow part and the tissue blood flow on the upstream side of each narrow part by an FFR simulation. Each narrow part is located on the inner wall of the culprit vessel specified by the culprit vessel specifier 108. The FFR calculator 109 divides the calculated tissue blood flow on the downstream side of a narrow part by the calculated tissue blood flow on the upstream side of the narrow part, thereby calculating the FFR (step S10).

Next, the culprit stenosis specifier 110 specifies a narrow part whose FFR calculated by the FFR calculator 109 is smaller than a threshold as a culprit stenosis (step S11). The connection position determiner 113 determines a connection position on the downstream side of the culprit stenosis based on the FFR drop level, the inner diameter of the blood vessel, the state of the blood vessel wall, and the like in the culprit vessel (step S12).

Figure 6:
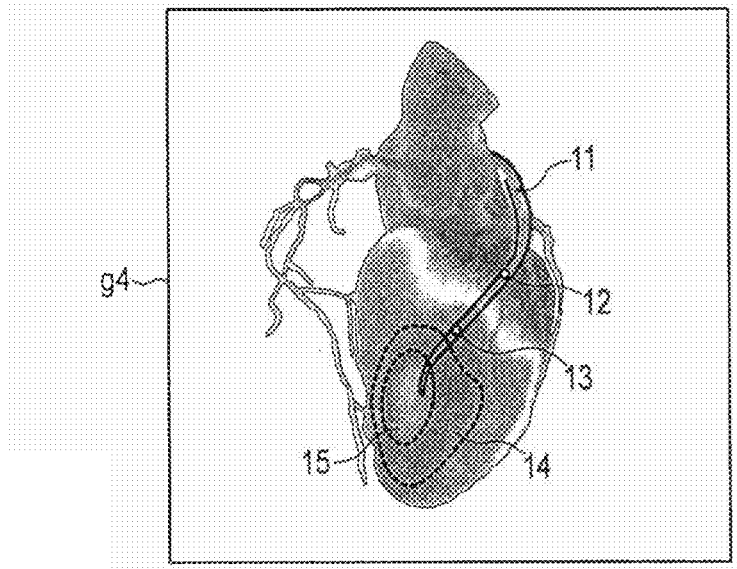
FIG. 6 is a schematic view showing an example of a three-dimensional image of a culprit vessel displayed on a display 112 shown in FIG. 1.
Figure 7:
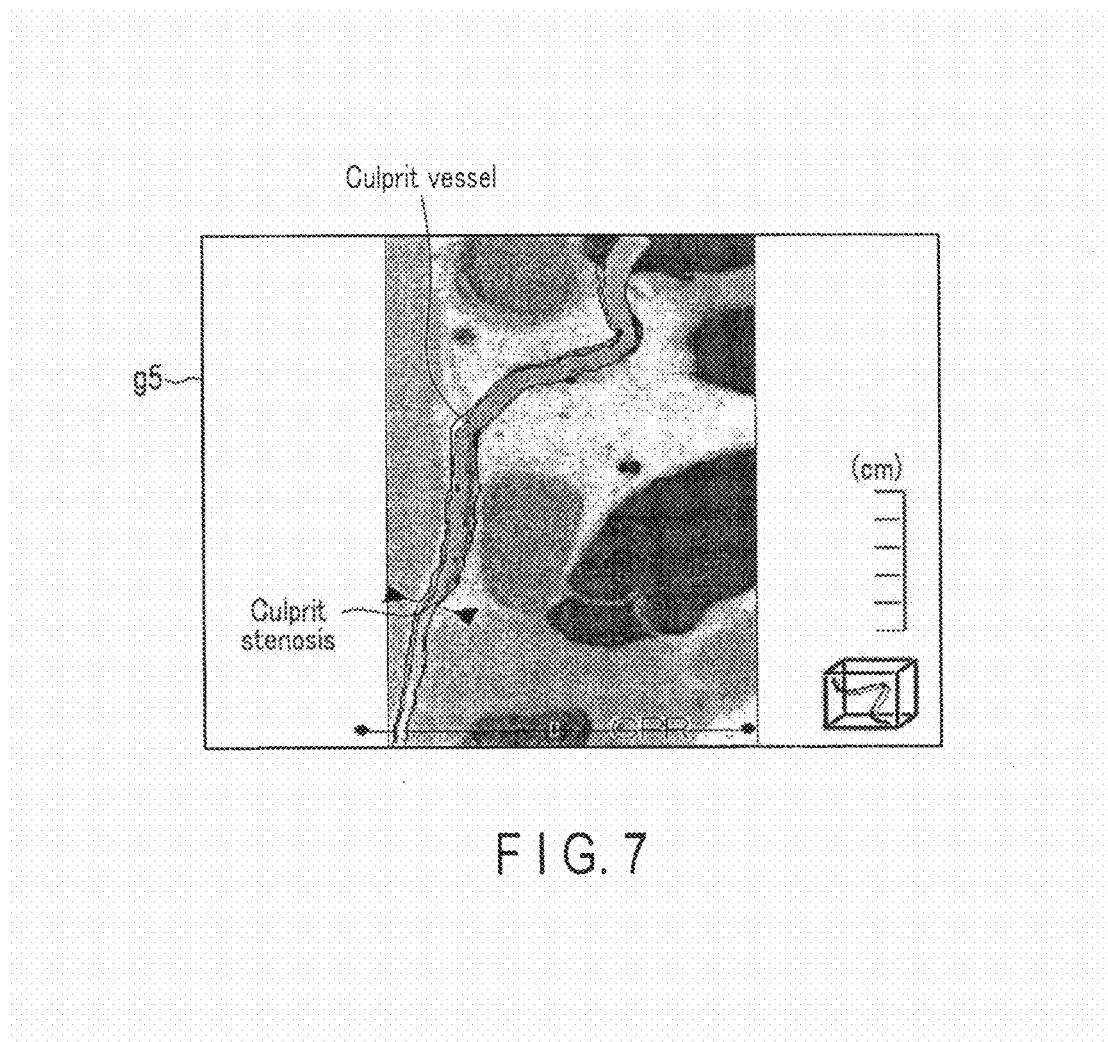
FIG. 7 is a schematic view showing an example of a two-dimensional image of the culprit vessel displayed on the display 112 shown in FIG. 1.

The display 112 displays a plurality of markers representing the culprit vessel 11, the culprit stenosis 12, and the FFR, which are generated by the marker generator 111 and superimposed on a three-dimensional image g4 or a two-dimensional image g5 derived from the volume data, as shown in, for example, FIGS. 6 and 7 (step S13). The Stenosis 13 is also shown in FIG. 6. The territory map of culprit vessel 14 and the ischemic region 15 may be shown in FIG. 6.

Figure 8:
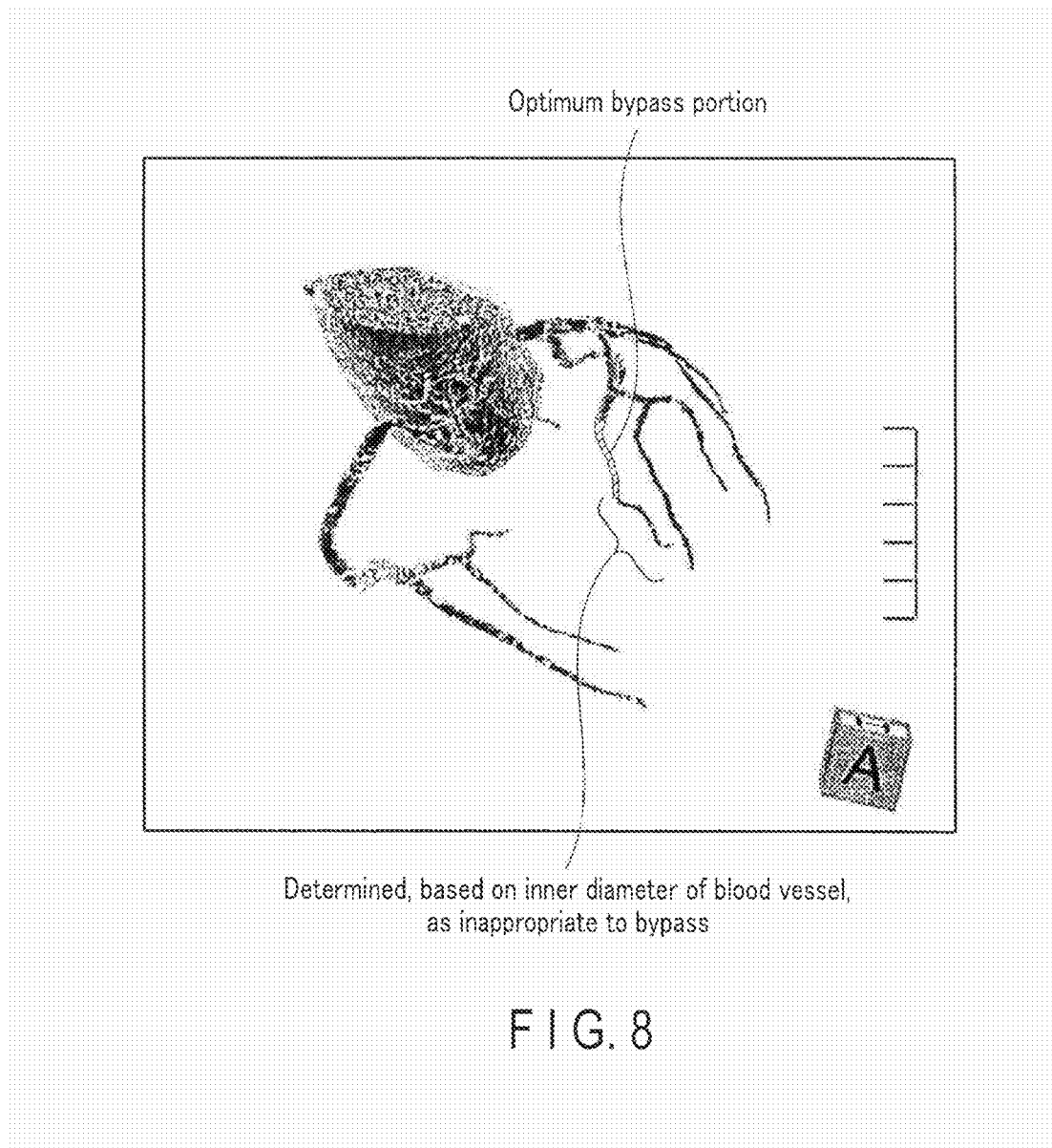
FIG. 8 is a view showing an example of a three-dimensional image including a connection position indicated by a marker.

The display 112 also displays a marker representing the connection position, which is generated by the marker generator 111 and superimposed on the three-dimensional image g4 or the two-dimensional image g5 derived from the volume data, as shown in, for example, FIG. 8.

Note that in FIG. 8, since the inner diameter of the blood vessel on the downstream side of the connection position is so thin (for example, 1.5 mm or less) as not to satisfy the criterion, this portion is determined as inappropriate to bypass and excluded from the color mapping display target.

With the above-described arrangement, the connection position for CABG can visually be presented to the user (for example, doctor), as shown in, for example, FIG. 8. Hence, the use can set the joint of the graft vessel to an appropriate portion. It is also possible to reduce the possibility of human errors.

In this embodiment, the FFR calculator 109 calculates the FFR value by calculation on a simulation base. That is, since no invasive instrument such as a pressure wire is necessary, the burden on the patient at the time of inspection can be reduced. In addition, the doctor can noninvasively make the preoperative plan of CABG. Since the inspection method is noninvasive, this embodiment is also effective for confirming the postoperative progress as follow-up.

Note that in this embodiment, FIGS. 6, 7, and 8 illustrate examples of images displayed by the display 112. However, images displayable by the display 112 are not limited to these. For example, a CPR image shown in FIG. 9 or an SPR (stretched CPR) image shown in FIG. 10 can also be displayed on the display 112.

Figure 9:
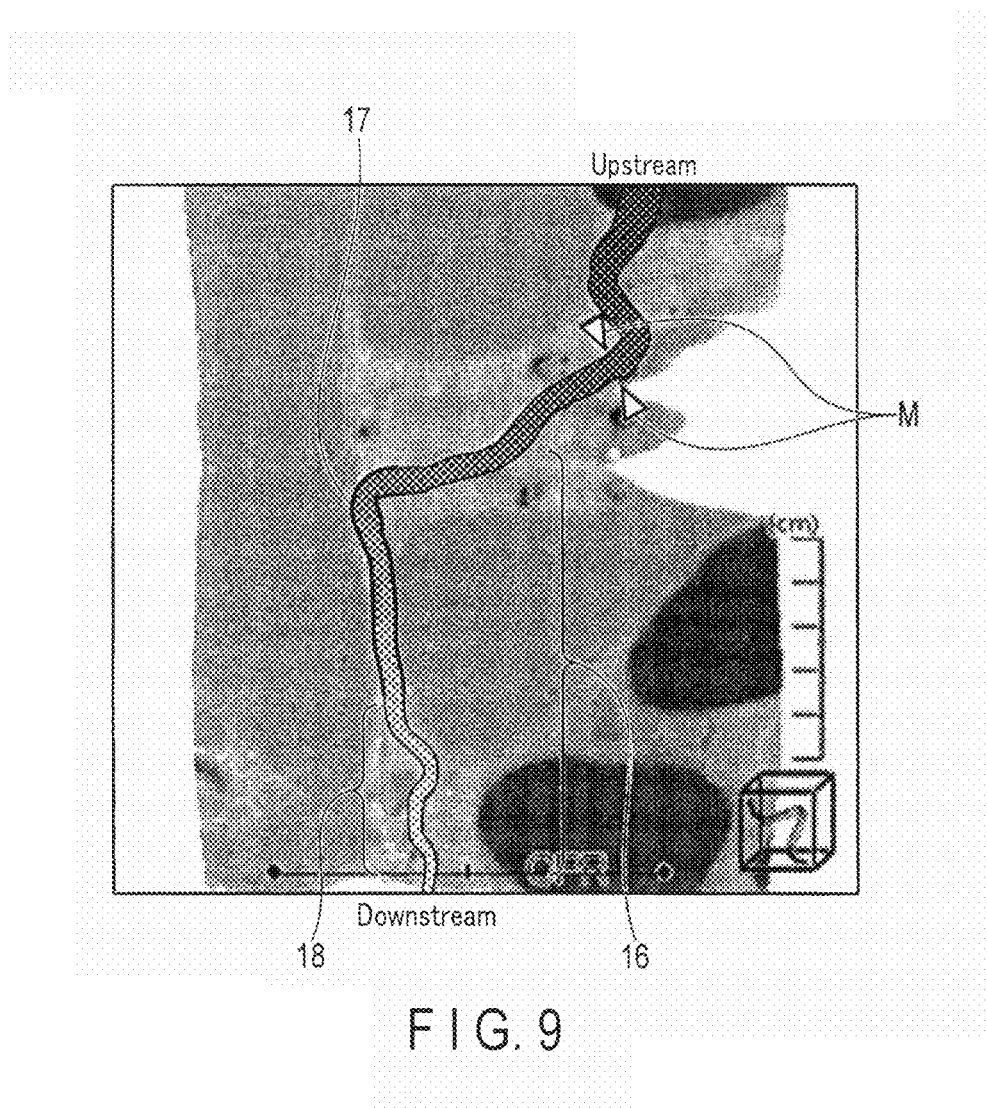
FIG. 9 is a view showing an example of a CPR image including a connection position indicated by a marker.

In the CPR image shown in FIG. 9, the FFR values are displayed by color mapping along a blood vessel. FFR values on the downstream side of a marker are lower than those on the upstream side of the marker but are stable. That is, the FFR drop level changes a little in region 16. Hence, this portion 17 is a connection position candidate. However, the inner diameter of the blood vessel is too small at the most downstream portion (region 18), and therefore, this portion is inappropriate as the connection position. The SPR image shown in FIG. 10 indicates the same as described above. In FIG. 10, the region 19 may be a connection position candidate. In region 22, the FFR drop level changes a little. However, in region 21, the inner diameter of the blood vessel is too small at the most downstream portion.

The doctor can recognize the optimum connection position of the graft vessel before thoracotomy by referring to these images.

According to the medical image processing apparatus 10 of the embodiment, the connection position can further be narrowed down based on the blood vessel elasticity as well. The elasticity coefficient is an index representing a so-called blood vessel wall hardness. A blood vessel whose elasticity coefficient is too low is too soft and may rupture at the time of operation. Conversely, a blood vessel whose elasticity coefficient is too high is too hard and may cause arteriosclerosis. This blood vessel is also inappropriate as the joint of the graft vessel.

Figure 11:
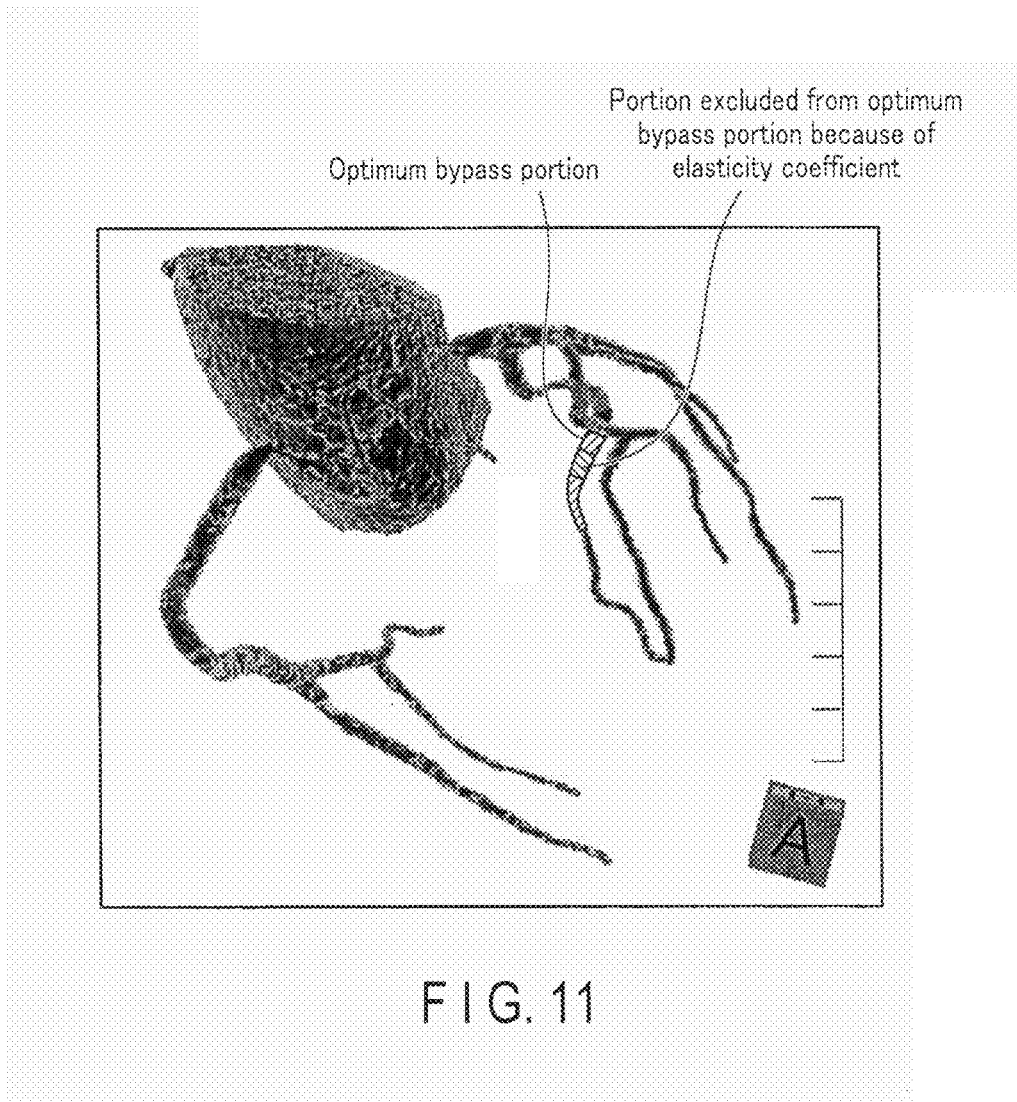
FIG. 11 is a view showing an example of a three-dimensional image representing that a region where the elasticity coefficient does not satisfy the criterion is excluded from connection position candidates.

FIG. 11 is a view showing an example of a three-dimensional image representing that a region where the elasticity coefficient does not satisfy the criterion is excluded from connection position candidates. The blood vessel elasticity is estimated by an FFR simulation of the FFR calculator 109 or by analyzing data from 4D-CT. When the connection position is determined in consideration of this finding, it is possible to avoid a portion that has an excellent FFR vale but is inappropriate as the joint of a blood vessel and also improve the treatment result.

According to the medical image processing apparatus 10 of the embodiment, details of the risk distribution at the connection position can be displayed by, for example, color mapping.

FIG. 12 is a view showing an example of a three-dimensional image representing a connection position including a risk distribution. The medical image processing apparatus 10 according to the embodiment analyzes CT volume data, thereby obtaining various risk factors such as the FFR, the inner diameter of a blood vessel, the state of a blood vessel wall, and the positional relationship between a blood vessel and a narrow part.

The display controller 114 displays a risk distribution including the risk factors on the display 112 while using different colors for the respective items at the connection position. This display method allows the doctor to recognize, at a glance, detailed information representing that, for example, a portion is safe but is not absolutely recommended as a connection position. The risks may be converted into scores, and colors corresponding to the scores may be mapped on the screen.

According to the medical image processing apparatus 10 of the embodiment, it is also possible to display the connection position in combination with another index.

Figure 13:
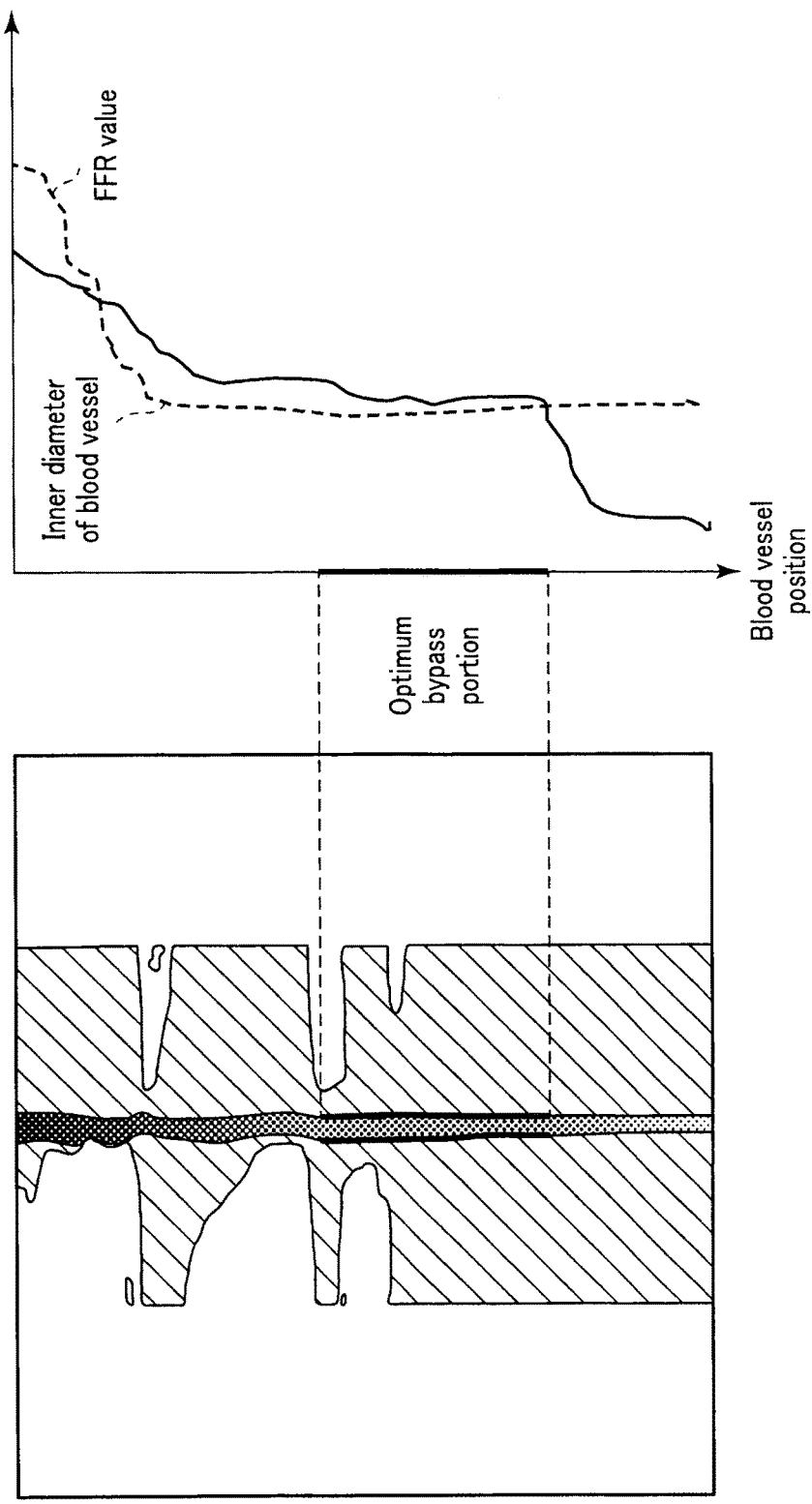
FIG. 13 is a view showing an example of an SPR image that displays an FFR value and the inner diameter of a blood vessel in combination with a connection position.
Figure 14:
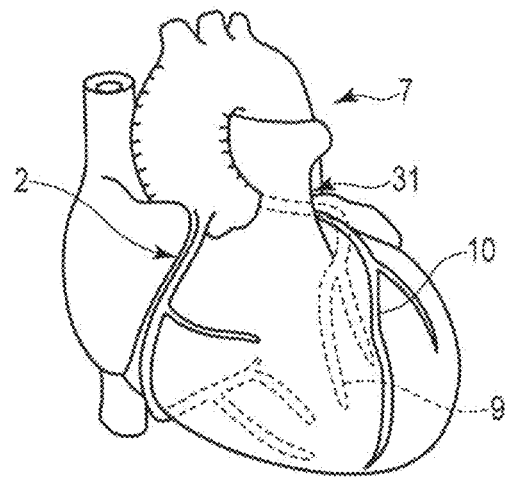
FIG. 14 is a schematic view for explaining the principle of CABG.
Figure 15:
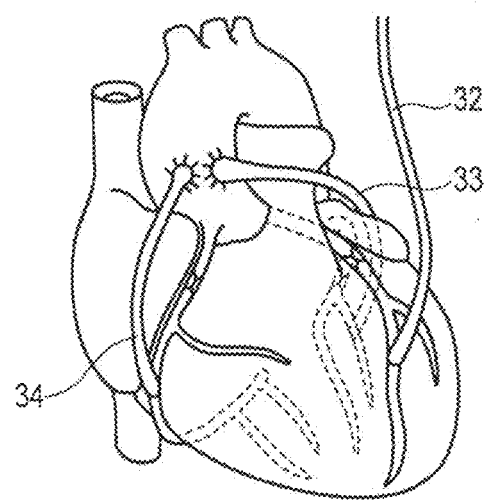
FIG. 15 is a schematic view for explaining the principle of CABG.
Figure 16:
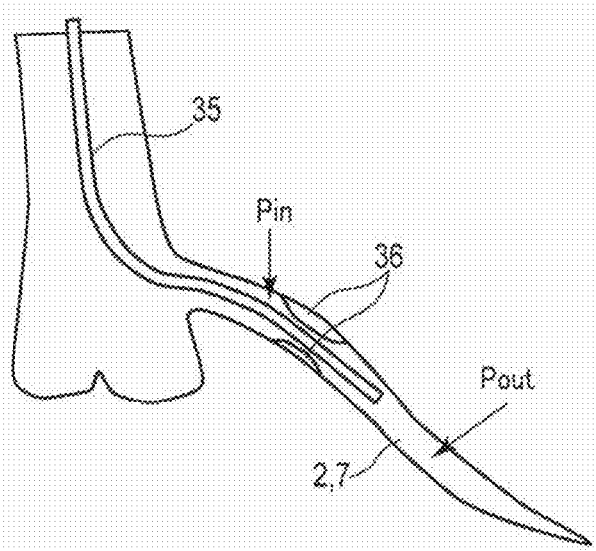
FIG. 16 is a schematic view for explaining FFR.

FIG. 13 is a view showing an example of an SPR image that displays an FFR value and the inner diameter of a blood vessel in combination with a connection position. The image shown in FIG. 13 is displayed on the display 112 mainly under the control of the display controller 114. As shown in FIG. 13, the FFR values and the inner diameters of a blood vessel are expressed along a blood vessel as graphs in combination of the display of the connection position. The graph of the solid line represents the inner diameter of the blood vessel. The graph of the dotted line represents the FFR. Only one of the graphs may be displayed.

When various kinds of information are displayed in accordance with the SPR image, a lot of pieces of information can be notified to the doctor. It is also possible to add information (thickness, hardness level, plaque thickness, and the like) about the blood vessel wall.

According to the medical image processing apparatus 10 of the embodiment, when an input of selection of a culprit vessel, culprit stenosis, or connection position is received from an input interface (not shown) such as a mouse, keyboard, or touch panel upon displaying a desired three-dimensional image on the display 112, the three-dimensional image can automatically be rotated to an angle easy to observe the selected culprit vessel, culprit stenosis, or connection position.

Hence, according to the embodiment, it is possible to provide a medical image processing apparatus capable of accurately showing an appropriate connection position.

Note that the present invention is not limited to the above-described embodiment. For example, in the embodiment, CABG for coronary arteries of a heart has been considered. The present invention can be applied to the preoperative plan of all diseases in a cerebral artery or other arteries to which a blood vessel bypass operation is applicable.

In the embodiment, the FFR calculator 109 calculates an FFR by the above-described calculation method. However, the FFR calculation method is not limited to this. Any method capable of calculating an FFR corresponding to each narrow part can appropriately be applied as the FFR calculation method used by the FFR calculator 109. For example, the simulation need not always be a 2D simulation but may be a 3D simulation.

In the embodiment, an FFR is calculated by an FFR simulation. Instead, an FFR obtained by the Gradient-method may be used. The Gradient-method uses the possibility that a blood flow and a CT value correlate with each other. This method can be an effective method for obtaining a quantitative value such as an FFR depending on future studies.

The functions explained in the above embodiment can be implemented by one or a plurality of processing units. The processing units can be, for example, dedicated or general-purpose processor, circuit (circuitry), processing circuit (circuitry), operation circuit (circuitry), arithmetic circuit (circuitry), or Application Specific Integrated Circuit (ASIC), Simple Programmable Logic Device (SPLD), Complex Programmable Logic Device (CPLD), and Field Programmable Gate Array (FPGA).

Each processing unit may be implemented as a processor including an electronic circuit such as a memory. The processing unit can include a processor that functions by a program stored in a memory. The processing unit can include an application specific integrated circuit (IC) or a conventional circuit element to execute the above-described functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising: processing circuitry configured to
receive a three-dimensional image regarding coronary arteries in a cardiac region and perfusion information regarding a cardiac muscle in the cardiac region;
extract an ischemic region regarding the cardiac muscle based on the perfusion information;
extract a plurality of coronary arteries from the three-dimensional image;
automatically determine a target vessel among the extracted coronary arteries based on a positional relationship between the extracted ischemic region and the extracted coronary arteries;
calculate a distribution of a pressure index of a blood flow in the target vessel; and
automatically determine a position to join a bypass vessel on the target vessel based on the distribution of the pressure index at the target vessel.

2. The medical image processing apparatus of claim 1, wherein the processing circuitry is further configured to determine the position based on a drop level of the pressure index.

3. The medical image processing apparatus of claim 2, wherein the processing circuitry is further configured to determine the position based on an inner diameter of the target vessel.

4. The medical image processing apparatus of claim 2, wherein the processing circuitry is further configured to determine the position based on an elasticity coefficient of the target vessel.

5. The medical image processing apparatus of claim 1, wherein the processing circuitry is further configured to determine the position based on an inner diameter of the target vessel.

6. The medical image processing apparatus of claim 1, wherein the processing circuitry is further configured to calculate a degree of fitness when the bypass vessel is joined to a predetermined portion of the blood vessel, and
the processing circuitry is further configured to cause a display to display a distribution of the degree of fitness at the predetermined portion.

7. The medical image processing apparatus of claim 1, wherein the pressure index comprises a myocardial fractional flow reserve.

8. The medical image processing apparatus of claim 1, wherein the processing circuitry is further configured to
extract a cardiac muscle region from the three-dimensional image in each of a plurality of phases; and
calculate perfusion information based on the extracted cardiac muscle regions.

9. The medical image processing apparatus of claim 1, wherein the processing circuitry is further configured to cause a display to display the determined position.

10. The medical image processing apparatus of claim 9, wherein the processing circuitry is further configured to cause the display to display at least one of a first graph representing the pressure index corresponding to the position and a second graph representing an inner diameter of the blood vessel corresponding to the position.

11. The medical image processing apparatus of claim 10, wherein the processing circuitry is further configured to cause the display to display at least one of the first graph and the second graph together with an image in which the position is visualized.

* * * * *